United States Patent [19]

Plueddemann

[11] 4,448,694

[45] May 15, 1984

[54] METAL EXTRACTION FROM SOLUTION AND IMMOBILIZED CHELATING AGENTS USED THEREFOR

[75] Inventor: Edwin P. Plueddemann, Midland, Mich.

[73] Assignee: Dow Corning Corporation, Midland, Mich.

[21] Appl. No.: 299,416

[22] Filed: Sep. 4, 1981

[51] Int. Cl.$^3$ .................. B01D 15/04; C02F 1/42; C08L 83/06; C07F 7/10
[52] U.S. Cl. .................. 210/682; 210/688; 556/400; 556/424; 423/6; 423/658.5
[58] Field of Search .............. 210/682, 688; 556/400, 556/424; 423/6, 658.5

[56] References Cited

U.S. PATENT DOCUMENTS

| | | | |
|---|---|---|---|
| 3,715,339 | 2/1973 | Rainer | 210/688 X |
| 3,886,080 | 5/1975 | Schucker et al. | 252/176 |
| 4,071,546 | 1/1978 | Plueddemann | 556/418 |
| 4,167,481 | 9/1979 | Cremers et al. | 210/688 X |
| 4,203,952 | 5/1980 | Hancock et al. | 423/6 |
| 4,238,328 | 12/1980 | Bowes et al. | 210/688 |
| 4,333,847 | 6/1982 | Tran et al. | 252/629 |

FOREIGN PATENT DOCUMENTS

| | | | |
|---|---|---|---|
| 18102 | 10/1980 | European Pat. Off. | 556/424 |
| 1238093 | 7/1971 | United Kingdom | 556/424 |
| 1530039 | 10/1978 | United Kingdom | 556/424 |

OTHER PUBLICATIONS

Chem. Abstr. #91:108,695y, Dvorak, et al., "Carbofunctional Organosilicon Derivatives of Tetraethylenepentamine", Czech Patent No. 177,563, 3/15/79, vol. 91, 1979.

Leyden, D. E., et al., *Analytical Chemistry*, vol. 47 (Aug. 1975), pp. 1612–1617.

Leyden, D. E., et al. "Structural Studies of Immobilized Ethylenediamine as a Concentrating Agent for Molybdate and Tungstate," Anal. Chim. Acta., vol. 100 (1978), pp. 845–854.

*Primary Examiner*—Deborah L. Kyle
*Assistant Examiner*—Matthew A. Thexton
*Attorney, Agent, or Firm*—R. L. McKellar

[57] ABSTRACT

What is disclosed are novel metal chelating agents which are bonded to inorganic substrates to immobilize them. An example of such a metal chelating agent is $(CH_3O)_3Si(CH_2)_3NH(CH_2CH_2NH)_2(CH_2)_3Si(OCH_3)$. An example of an inorganic substrate is a silica gel.

22 Claims, No Drawings

METAL EXTRACTION FROM SOLUTION AND IMMOBILIZED CHELATING AGENTS USED THEREFOR

BACKGROUND OF THE INVENTION

This invention was made with Government support under NSF Grant No. CHE-7823123 awarded by the National Science Foundation. The Government has certain rights in this invention.

The present invention deals with new and novel chelating agents which can be immobilized on inorganic solids and used to chelate metals from solution.

It is well known in the art to treat inorganic solids with hydrolyzable organosilanes to bond the organosilanes to the inorganic solid surfaces. For example, British Pat. No. 1,530,039 published Oct. 25, 1978, and assigned to the British Petroleum Company Limited, shows the used of polyamines bonded to inorganic solids by the use of an organosilane coupling agent. The organosilane coupling agent is described preferably as alpha-chloropropyl-trimethoxysilane and the polyamine as $N(CH_2CH_2NH_2)_3$. Leyden, et al., Anal. Chem., 47(a), pp. 1612 to 1617, August 1975, shows the use of aminoalkyltrimethoxysilanes as treatments for silica gel to give a silica having aminoalkylsilyl groups on the surface which are subsequently derivatized to the corresponding dithiocarbamate to give chelating groups on the surface of the silica.

Plueddemann, U.S. Pat. No. 4,071,546, issued Jan. 31, 1978, prepared carboxymethyl containing polyaminosiloxanes which were bonded to siliceous supports which were subsequently used as metal chelating agents and Hancock et al., in U.S. Pat. No. 4,203,952, issued May 20, 1980, and assigned to the British Petroleum Company, shows the use of silane coupling agents to bond various amine functional chelating compounds to inorganic solids.

G. D. Schucker et al., in U.S. Pat. No. 3,886,080, issued May 27, 1975, shows the use of silane coupling agents to immobilize certain chelating agents on inorganic solids. Specifically, the compound 8-hydroxyquinoline is shown as one of the chelating agents that can be bound to inorganic solids by their method.

Finally, the inventor in this application, E. P. Plueddemann, has disclosed in a copending U.S. patent application, Ser. No. 279,388, filed July 1, 1981, that 8-hydroxyquinoline chelating agents could be bonded by novel means to the surface of inorganic solids which result in new immobilized chelating substances which have durability on the inorganic solid substrate thereby giving the chelating agent extended chelating capacity.

Percolation of dilute heavy metal ion solutions through silylated silica has been used as an analytical method for concentrating the metal ion for estimation by X-ray fluorescence (D. E. Leyden, M. L. Steele and B. B. Jablonski, Anal, Chem. Acta, 100 549 (1978)). In these methods, amine functional silanes were used to bond chelating agents to the silica surface. Materials such as $(CH_3CH_2O)_3Si(CH_2)_3NH_2$ and $(CH_3O)_3Si(CH_2)_3NH(CH_2)_2NH_2$ have been preferred silylating agents and these materials give almost quantitative yields when used as chelating agents themselves. Capacity for metal ions is proportional to surface area of the filler. These hydrolyzed hydrophilic silanes when deposited under mild conditions on siliceous surfaces are not tightly bonded to the surface through the surface silanols. Siloxane bonds formed between the coupling agent and the siliceous surface are hydrolyzable and if the hydrolyzed hydrophilic silane is a monomer or an uncrosslinked oligomer, the coupling agent is displaced relatively easily from the surface. Crosslinking such monomers or oligomers while on a silica surface, such as by heating, is not a useful method of imparting durability to the treated surface since for the metal ion removal application, the reactivity with the metal ions is reduced or lost.

The hydrophilic diamine group on a silica surface becomes even more hydrophilic in acid solutions such as are used to elute metals from chelate-silylated surfaces.

Further, as it has already been pointed out by Schucker, supra, inorganic solid substrates for immobilization of the chelating agents are preferred over that of organic carriers because the inorganic carriers are biologically stable; they do not tend to swell or shrink with changing conditions of pH and, such compositions can be sterilized without degradation (see Column 2, line 15 et seq. of Schucker).

It would thus appear that it would be desirable to have the stability of the inorganic substrates and a chelating agent which has enhanced durability and strong chelating properties over that of the above discussed prior art materials.

It is one object of this invention to provide novel silicon-containing chelating agents which are useful for removing heavy metal ions from solutions.

It is another object of this invention to provide immobilized chelating agents which have durability in use.

These and other objects will become obvious after consideration of the following disclosure and claims.

THE INVENTION

In one aspect, this invention deals with a method for preparing an immobilized chelating agent. The chelating agent is immobilized by reacting an organofunctional silane, as a bis compound, with an inorganic substrate. Thus, this invention deals with a method for preparing an immobilized chelating agent which comprises treating an inorganic solid substrate with a silylating agent which is a compound of the formula $(RO)_3SiQNH(CH_2CH_2NH)_xQSi(OR)_3$ where x has a value of 2, 3, or 4, R is a methyl, ethyl, propyl or butyl radical and Q is propylene or butylene.

It should be noted that the general formula contemplates very few specific compounds. The polyamine precursors for the bis silanes are commercial products and are obtainable from many sources one of which is The Dow Chemical Co., Midland, Mich., USA. The materials can be purchased under the names of diethylenetriamine, triethylenetetramine and tetraethylenepentamine.

It should be noted that these materials are not pure amines by virtue of the methods by which they are manufactured. For purposes of this invention, the inventor means to include commercial polyamines, such as those named above, even though it is recognized that such amines are not pure. For example, it is known from the sales literature that tetraethylenepentamine is composed of the following:

| MAJOR COMPONENTS: | % |
|---|---|
| $H_2N(CH_2CH_2NH)_2-CH_2CH_2NH_2$ | 2 |

-continued

| | |
|---|---|
| H₂NCH₂CH₂NHCH₂CH₂N⟨⟩NH | 3 |
| HN⟨⟩NCH₂CH₂N⟨⟩NH | 2 |
| H₂NCH₂CH₂NCH₂CH₂NHCH₂CH₂NH₂<br>\|<br>CH₂CH₂NH₂ | 10 |
| H₂N(CH₂CH₂NH)₃—CH₂CH₂NH₂ | 40 |
| H₂NCH₂CH₂N⟨⟩NCH₂CH₂NHCH₂CH₂NH₂ | 20 |
| H₂N⟨⟩NCH₂CH₂NHCH₂CH₂NHCH₂CH₂NH₂ | 7 |
| (5 isomers) | 16 |

| AMINE CONTENT: | % N | Meq./g | mg. KOH/g |
|---|---|---|---|
| Primary Amine | 13.8 | 9.9 | 530 |
| Secondary Amine | 14.4 | 10.3 | 577 |
| Tertiary Amine | 5.5 | 3.9 | 220 |
| Total Basic N | 33.7 | 24.1 | 1327 |

AVERAGE MOLECULAR WEIGHT = 201 g/mol.

The polyamines are reacted with chloroalkylsilanes in order to prepare the bis silane compounds of this invention.

Thus, for example, chloropropyltrimethoxysilane is reacted with the polyamine in a ratio of at least two moles of chloropropyl to one mole of polyamine (i.e. two equivalents of —NH₂).

2(CH₃O)₃Si(CH₂)₃Cl + H₂N(CH₂CH₂NH)₃—CH₂CH₂NH₂→(CH₃O)₃Si(CH₂)₃NH(CH₂CH₂NH)₄(CH₂)₃Si(OCH₃)₃. This general reaction is known from Dvorak, Mojmir, et al. in Czechslovakian Pat. No. 177,563 (Mar. 15, 1979) (CA 91:108695y) except that the disclosure therein teaches a 1:1 mole ratio of alkylchloro compound to the polyamine (2 equivalents —NH₂)

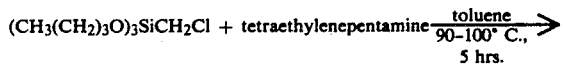

For purposes of this invention, the value of x is 2, 3, or 4 and R is selected from the radicals methyl, ethyl, propyl and butyl. Most preferred is the methyl group.

Q is a linking group selected from propylene and butylene. Contemplated within the scope of the Q group are the iso derivatives and the preferred iso derivative is

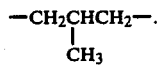

For purposes of this invention, the crude product is generally used to treat the inorganic solid substrate and the water found on such substrates hydrolyzes the trialkoxy groups, in situ, during the substrate treatment.

The method is carried out by simply mixing the bis silanes of this invention with the inorganic solid, usually in a water-insoluble solvent, and warming to a boiling stage for 1–2 hours. The concentration of the organosilicon compound in the treating solution is usually one-half to about five weight percent. The object is to cap all available hydroxyl groups on the surface with the organosilicon compound. As is obvious therefore, the inorganic solids that are useful in this invention are those which have hydroxyl groups on their surfaces. Further, such inorganic solids must be insoluble in water and solvents (although they should be dispersable therein) since applications for such materials within the scope of this invention are in various aqueous and solvent solutions. Examples of such inorganic solids are alumina, bentonite, sand, glass, silicas and silica gels. It is preferred for purposes of this invention that the inorganic solid be finely divided. Finely divided for purposes of this invention means any particulate material having an average diameter of less than 10 mm. The treated inorganic solid is then filtered to remove the liquid portions and washed with fresh solvent and thereafter dried in an air circulating oven.

Thus, this invention also contemplates a product which is an immobilized chelating agent bound to an inorganic solid which is prepared by treating an inorganic solid substrate with a silylating agent which is a compound of the formula (RO)₃SiQNH(CH₂CH₂NH)ₓQSi(OR)₃ where x has a value of 2, 3, or 4, R is a methyl, ethyl, propyl or butyl radical and Q is propylene or butylene.

In addition, this invention contemplates a method of removing heavy metal ions from solution which method comprises contacting a solution containing heavy metal ions with a silylated substrate prepared by treating an inorganic solid substrate with a silylating agent which is a compound of the formula (RO)₃SiQNH(CH₂CH₂NH)ₓQSi(OR)₃ where x has a value of 2, 3, or 4, R is a methyl, ethyl, propyl or butyl radical and Q is propylene or butylene.

The chelating product is ready for use after drying and it can be stored in this manner. When used, the dried product is typically re-dispersed in the metal containing solution that is to be treated. Typically, this treatment is carried out at room temperature but it can also be carried out at higher temperatures. The pH of the treating solution may have to be adjusted in order to maximize the chelating capability of the product. A pH of 6.5 to 7.5 is considered to be advantageous for most applications.

The chelating substrate does not have infinite activity because the metal ions are removed from the metal ion solution relative to the amount of chelate available and this in turn is dependent on the amount of the chelate bound to the inorganic solid which is in turn dependent on the surface area of the inorganic solid and the number of hydroxyl groups available for coupling with the alkoxysilyl groups of the inventive bis silanes. Further, the extent to which metal ion solution can be cleaned of metal ions is proportionate to the amount of treated substrate that comes in contact with metal ions. It therefore becomes advantageous in most applications to utilize, glass or plastic columns packed with the finely divided treated chelating substrate and pass the solution to be treated through such columns. However, batch treatments can be used with the chelating substrates of this invention.

When the substrate loses its activity for removing metals it may be discarded or the substrate may be reactivated by the use of mineral acid. One such method requires contacting the metal chelated substrate with an aqueous acid solution such as $HNO_3$, followed by separation of the aqueous acid solution from the substrate. The metal can then be recovered or discarded as desired.

Heavy metal ions contemplated within this invention are the transition elements (series 3b, 4b, 5b, 6b, 7b, 8b, and 1b of the periodic table) and the zinc family (series 2b of the periodic table). Especially contemplated within the scope of this invention are the lanthanides and actinides. This invention is especially useful for removal of the more commonly used metals such as copper, platinum, nickel, gold, silver, and iron.

The following examples are shown to illustrate the invention and are not intended to define the scope thereof.

EXAMPLE 1

Bis-trimethoxysilylpropyltriethylenetetramine (TETA)

In this reaction, the amine precursor acts as its own HCl acceptor.

Into a 500 ml, 3-necked round-bottomed glass flask were weighed 75 gms (0.5 moles) of commercial triethylenetetramine, 200 gms. (1.0 moles) of $(CH_3O)_3Si(CH_2)_3Cl$ and 25 gms. of $CH_3OH$. The flask was equipped with a motor driven stirrer, thermometer and reflux condenser. The reaction mass was heated to reflux and when the stirrer was stopped there was observed two layers. $CH_3OH$, 100 gms., was added to give a homogeneous material. The reaction mass was heated overnight (about 16 hrs.) at reflux. Upon cooling, a titration for $Cl^-$ showed about 0.88 equivalents of the $Cl^-$. The reaction was heated at reflux for an additional 8 hours after about 250 gms. of $CH_3OH$ had been added. The reaction was essentially complete at this time. The crude reaction product gave a hazy solution in water and in alcohols but it gave a clear solution in dilute acetic acid.

EXAMPLE 2

Bis-trimethoxysilylpropyltetraethylene pentamine (TEPA)

In a reaction flask, equipped as in example 1, there was placed 20 gms. (0.1 mole plus 10% mole excess) of tetraethylenepentamine, 40 gms. (0.2 moles) of distilled $(CH_3O)_3Si(CH_2)_3Cl$ and 40 gms. of $CH_3OH$. This mixture was refluxed (about 65° C.) for 3 hours where a titration showed 0.07 equiv. of $Cl^-$. The reaction was continued at reflux for an additional 21 hours whereupon the reaction mass titrated at 0.19 equiv. of $Cl^-$. A crude sample of this material (10 weight %) gave an initial hazy solution in acidic water or basic water but the material cleared within about 30 minutes to give stable solutions.

EXAMPLE 3

Bis-trimethoxysilylpropyldiethylene triamine (DETA)

In a manner similar to the above examples, a bis trimethoxysilylpropyldiethylenetriamine was prepared. The precursor amine was about 95% pure linear material.

EXAMPLE 4

Bis-trimethoxysilylpropylethylene diamine (EDA)

In a manner similar to that shown in examples 1 and 2 above, 44 gms. of $(CH_3O)_3Si(CH_2)_3NH(CH_2)_2NH_2$ and 40 gms. of $(CH_3O)_3Si(CH_2)_3Cl$ were mixed together and warmed to 140° C. whereupon the reaction exothermed to 200° C. The reaction mass was heated at 140° C. for about 2 hours and then cooled and diluted using 168 gms. of $CH_3OH$. After removal of HCl as an ethylenediamine salt, the crude product was distilled to recover a center cut boiling at 160° C. at 0.5 mm Hg, $d_4^{25}=1.048$, $N_D^{25}=1.4462$.

Note that this material does not fall within the scope of the instant invention but is included as a comparison to show that it is not useful as a chelating agent when immobilized on a solid substrate.

EXAMPLE 5

The materials from the examples above were evaluated as immobilized chelating agents for heavy metals.

A silica gel, Davison grade 62 was used in this evaluation. Grade 62 is available commercially from Davison, a division of W. R. Grace Co., 10 East Baltimore St., Baltimore, MD. This material has a pore volume of 1.15 cc/gms; average pore diameter of 140 Angstroms; surface area of 340 $M^2$/gm. and a mesh size of 60-200 (U.S. Standard Mesh).

Small portions of the silica gel and the bis silanes were mixed together and warmed to a gentle boil for 1 hour. The silanes were used as 2% solutions in toluene. The treated silica was recovered by filtration and washed with fresh toluene and then dried for 2 hours in a 60° C. air-convection oven.

Five gram portions of treated silica were mixed with 50 ml of 1 weight % $Cu++$ (chloride) solution and adjusted to pH 7 with ammonia. After mixing for 15 minutes, the treated silica was filtered and washed 10 times with deionized water. The washed silica was then stirred with 30 ml. of 1 weight % $HNO_3$ for 30 minutes. A portion of the $HNO_3$ was analyzed for $Cu++$ by atomic absorption. The acid eluted silica was rinsed with water and stored under water, as shown in the table below. This was one cycle. The treated silica was then recycled with more copper solution. Cycles were repeated after 1, 4, and 45 days storage in water. Copper capacity is reported as ppm $Cu++$ in the 30 ml nitric acid solution. Copper concentration of 1000 ppm is equivalent to a capacity of 0.1 milliequivalents of copper per gram of silica. Copper capacities are shown in Table I.

TABLE I

| Treatment on Silica Gel | Copper Capacity of Silylated Silica Gel | | | |
|---|---|---|---|---|
| | $Cu++$ in $HNO_3$ Acid Rinse (ppm) | | | |
| | 1st Cycle | 2nd Cycle 1 Day Later | 3rd Cycle 4 Days Later | % Retention After 3rd Cycle |
| Untreated Silica | 114 | 50 | 51 | — |
| *EDA | 113 | 20 | 20 | 17.7 |
| DETA | 1590 | 910 | 740 | 46.5 |

TABLE I-continued

| Treatment on Silica Gel | Copper Capacity of Silylated Silica Gel | | | |
|---|---|---|---|---|
| | Cu++ in HNO$_3$ Acid Rinse (ppm) | | | |
| | 1st Cycle | 2nd Cycle 1 Day Later | 3rd Cycle 4 Days Later | % Retention After 3rd Cycle |
| TETA | 1025 | 625 | 475[1] | 46.3 |
| TEPA | 538 | 356 | 270 | 50.2 |
| *(CH$_3$O)$_3$Si(CH$_2$)$_3$NH(CH$_2$)$_2$NH$_2$ | 1100 | 338 | 260[2] | 23.6 |
| *{ (CH$_3$O)$_3$Si(CH$_2$)$_3$NH(CH$_2$)$_2$NH$_2$ blended with (CH$_3$O)$_3$Si(CH$_2$)$_2$Si(OCH$_3$)$_3$ | 525 | 235 | 180 | 34.3 |

*Outside scope of invention, comparison samples
[1] After 45 days (4th cycle) = 260 ppm Cu++
[2] After 45 days (4th cycle) = 62 ppm Cu++

That which is claimed is:

1. A method for preparing an immobilized chelating agent which comprises treating an inorganic solid substrate with a silylating agent which is a compound of the formula (RO)$_3$SiQNH(CH$_2$CH$_2$NH)$_x$QSi(OR)$_3$ where x has a value of 2, 3, or 4, R is a methyl, ethyl, propyl or butyl radical and Q is propylene or butylene.

2. The product produced by the method of claim 1.

3. A method of removing heavy metal ions from solution which method comprises contacting a solution containing heavy metal ions with a silylated substrate of claim 2.

4. A method as claimed in claim 3 wherein the solution is aqueous, the substrate is siliceous mineral and the treating compound is (CH$_3$O)$_3$Si(CH$_2$)$_3$NH(CH$_2$CH$_2$NH)$_x$(CH$_2$)$_3$Si(OCH$_3$)$_3$.

5. A method as claimed in claim 4 wherein x is 2.

6. A method as claimed in claim 4 wherein x is 3.

7. A method as claimed in claim 4 wherein x is 4.

8. A method as claimed in claim 3 wherein the heavy metal ions are transition metal ions.

9. A method as claimed in claim 8 wherein the transition metal ions are lanthanides.

10. A method as claimed in claim 8 wherein the transition metal ions are actinides.

11. A method as claimed in claim 8 wherein the transition metal ion is copper.

12. A method as claimed in claim 8 wherein the transition metal ion is iron.

13. A method as claimed in claim 8 wherein the transition metal ion is cobalt.

14. A method as claimed in claim 8 wherein the transition metal ion is nickel.

15. A method as claimed in claim 8 wherein the transition metal ion is molybdenum.

16. A method as claimed in claim 8 wherein the transition metal ion is rhodium.

17. A method as claimed in claim 8 wherein the transition metal ion is silver.

18. A method as claimed in claim 8 wherein the transition metal ion is platinum.

19. A method as claimed in claim 8 wherein the transition metal ion is gold.

20. A method as claimed in claim 8 wherein the transition metal is manganese.

21. A method as claimed in claim 8 wherein the transition metal is titanium.

22. A method as claimed in claim 10 wherein the actinide is uranium.

* * * * *